(12) United States Patent
Huang et al.

(10) Patent No.: US 10,828,406 B2
(45) Date of Patent: Nov. 10, 2020

(54) CONCEALABLE BREAST PUMPING DEVICE

(71) Applicant: Shyh-Jer Huang, Tainan (TW)

(72) Inventors: Shyh-Jer Huang, Tainan (TW); Chieh-Wei Chiang, Tainan (TW); Kai Chang, Tainan (TW); Chia-Lung Chan, Douliu (TW); Hao-Cyuan Jhang, Taichung (TW)

(73) Assignee: Shyh Huang, Tainan (TW)

( * ) Notice: Subject to any disclaimer, the term of this patent is extended or adjusted under 35 U.S.C. 154(b) by 109 days.

(21) Appl. No.: 16/199,629

(22) Filed: Nov. 26, 2018

(65) Prior Publication Data

US 2019/0160211 A1    May 30, 2019

(30) Foreign Application Priority Data

Nov. 27, 2017 (TW) .............................. 106141091 A
May 28, 2018 (TW) .............................. 107118121 A

(51) Int. Cl.
*A61M 1/06* (2006.01)

(52) U.S. Cl.
CPC .............. *A61M 1/062* (2014.02); *A61M 1/06* (2013.01); *A61M 2209/088* (2013.01)

(58) Field of Classification Search
CPC .. A61M 1/06; A61M 1/062; A61M 2209/088; A61M 1/066; A61M 1/0072; A61M 1/0624; A61M 1/064
See application file for complete search history.

(56) References Cited

U.S. PATENT DOCUMENTS

| | | | | |
|---|---|---|---|---|
| 5,358,476 A | * | 10/1994 | Wilson | A61M 1/06 604/74 |
| 6,328,082 B1 | * | 12/2001 | Lafond | A61J 9/005 141/114 |
| 2002/0156419 A1 | * | 10/2002 | Silver | A61M 1/062 604/74 |
| 2006/0074379 A1 | * | 4/2006 | Hunt | A61J 9/005 604/74 |
| 2008/0275386 A1 | * | 11/2008 | Myers | A61M 1/062 604/74 |
| 2010/0179472 A1 | * | 7/2010 | Weston | A61M 1/0027 604/67 |
| 2014/0100520 A1 | * | 4/2014 | Yamashita | A61M 1/0072 604/74 |
| 2016/0287766 A1 | * | 10/2016 | Bambino | A61M 1/062 |

(Continued)

*Primary Examiner* — Rebecca E Eisenberg
(74) *Attorney, Agent, or Firm* — Muncy, Geissler, Olds & Lowe, P.C.

(57) ABSTRACT

A concealable breast pumping device is provided, including a primary unit, a squeezing unit, a milk collection bag, a stop valve unit, and a driving unit. The primary unit includes a channel, a protruding portion, and a concave portion. The protruding portion has a port. The port communicates with the channel. The inner wall of the concave portion has a spiral convex portion. The squeezing unit is covered on one end of the primary unit. One end of the milk collection bag is connected to the protruding portion, and the other end has an opening. The opening is gripped by a gripping tool. The stop valve unit is positioned in the milk collection bag. One end of the stop valve unit is connected to the protruding portion. The other end has a gap, and the gap is able to opened and closed movably.

9 Claims, 6 Drawing Sheets

(56) References Cited

U.S. PATENT DOCUMENTS

2016/0317728 A1* 11/2016 Lewis .................... A61M 1/062
2018/0043070 A1* 2/2018 Habig ................ A61M 39/1011
2018/0345171 A1* 12/2018 Hampton ........... B65D 75/5883

* cited by examiner

CONCEALABLE BREAST PUMPING DEVICE

CROSS-REFERENCE TO RELATED APPLICATION

This application claims priority from Taiwan Patent Application No. 107118121, filed on May 28, 2018 and No. 106141091, filed on Nov. 27, 2017, in the Taiwan Intellectual Property Office, the content of which is hereby incorporated by reference in its entirety for all purposes.

FIELD OF THE INVENTION

The present disclosure relates to a concealable breast pumping device, more particularly to a concealable breast pumping device designed to be integrated or miniaturized and made from a single material.

BACKGROUND OF THE INVENTION

Mother's milk is the most suitable natural food for a baby, providing the nutrients needed for a baby to grow. Mother's milk contains many nutrients, is easy to digest, has a high absorption rate and bioavailability, and burdens a baby least. Because of the advantages of feeding a baby with mother's milk, more and more women after giving birth choose to feed their babies with mother's milk.

When it is inconvenient for a mother to breastfeed a baby or a baby is bad at sucking milk from a mother's breast, a breast pumping device can be used to extract milk beforehand, and the milk may be frozen for a later use so that the milk after heating can be put in the nursing bottle to feed the baby. However, conventional breast pumping devices are composed of many components which are complicated in structure and large in size. These breast pumping devices with many components are also difficult to be disassembled for cleaning, thus easily causing sanitary problems.

In view of what is mentioned above, the inventor of the present disclosure has designed a concealable breast pumping device to improve deficiencies in terms of current techniques so as to enhance the implementation and application in industries.

SUMMARY OF THE INVENTION

In view of the aforementioned problems, the present disclosure aims to a concealable breast pumping device to solve the problems that can be encountered in prior art.

On the basis of the aforementioned purpose, the present disclosure provides a concealable breast pumping device, including a primary unit, a squeezing unit, a milk collection bag, a stop valve unit, and a driving unit. One end of the primary unit is concaved inward to form a channel. An outer edge of the primary unit extends outward to form a protruding portion. The protruding portion has a port. The port communicates with the channel. A center of the other end of the primary unit is concaved inward to form a concave portion. An inner wall of the concave portion has a spiral convex portion. The squeezing unit is regarded as a cover body structure and covered on one end of the primary unit. One end of the milk collection bag is connected to the protruding portion. The other end has an opening. Two sides of the opening respectively extend to form two extending portions. The two extending portions are gripped by a gripping tool selectively. The stop valve unit is positioned in the milk collection bag and one end of the stop valve unit is connected to the protruding portion. The other end has a gap, and the gap is able to opened and closed movably. The stop valve unit has a flow path. One end of the flow path communicates with the port, and the other end communicates with the gap. The main body of the driving unit respectively extends outward to form an engaging portion and a controlling portion. The engaging portion and the controlling portion are hollow structures. The inside of the engaging portion communicates with the inside of the controlling portion. The engaging portion is detachably jointed with the other end of the primary unit. The controlling portion is connected to an external device.

Preferably, when an internal gas of the controlling portion and the engaging portion is extracted by an external device, the one end of primary unit is shifted toward the inside of the engaging portion and drives the squeezing unit to generate a contraction.

Preferably, when the controlling portion and the inside of the engaging portion are pressure-released by an external device to supply gas, the one end of the primary unit is shifted toward an outside of the engaging portion and drives the squeezing unit to generate an expansion.

Preferably, the primary unit, the squeezing unit, the milk collection bag, and the stop valve unit are integrated.

Preferably, the primary unit, the squeezing unit, milk collection bag, and the stop valve unit are made of silica gel.

Preferably, the flow path is in a conical shape.

Preferably, the other end of the stop valve unit is in a flat shape.

Preferably, an inner wall on one side of the milk collection bag has a plurality of strip structures.

Preferably, an outer wall on one side of the milk collection bag has a plurality of hook rings.

As stated, the concealable breast pumping device in the present disclosure is designed by the integration of four components, namely the primary unit, the squeezing unit, the milk collection bag, and the stop valve unit, making the pumping device easy to clean by users. Moreover, under the conditions of an integrated design that miniaturizes the volume, users may use the pumping device on their breasts at anytime and anywhere, largely enhancing the users' convenience at using the pumping device.

DETAILED DESCRIPTION OF THE ILLUSTRATED EMBODIMENTS

To facilitate the review of the technique characteristics, contents, advantages, and achievable effects of the present disclosure, the embodiments together with the drawings are described in detail as follows. However, the drawings are used only for the purpose of indicating and supporting the specification, which is not necessarily the real proportion and precise configuration after the implementation of the present disclosure. Therefore, the relations of the proportion and configuration of the attached drawings should not be interpreted to limit the actual scope of implementation of the present disclosure.

The advantages, features, and technical methods of the present disclosure are to be explained in detail with reference to the exemplary embodiments and the figures for the purpose of being more easily to be understood. Moreover, the present disclosure may be realized in different forms, and should not be construed as being limited to the embodiments set forth herein. Conversely, for a person skilled in the art, the embodiments provided shall make the present disclosure convey the scope more thoroughly, comprehensively, and completely. In addition, the present disclosure shall be defined only by the appended claims.

Figure 1:
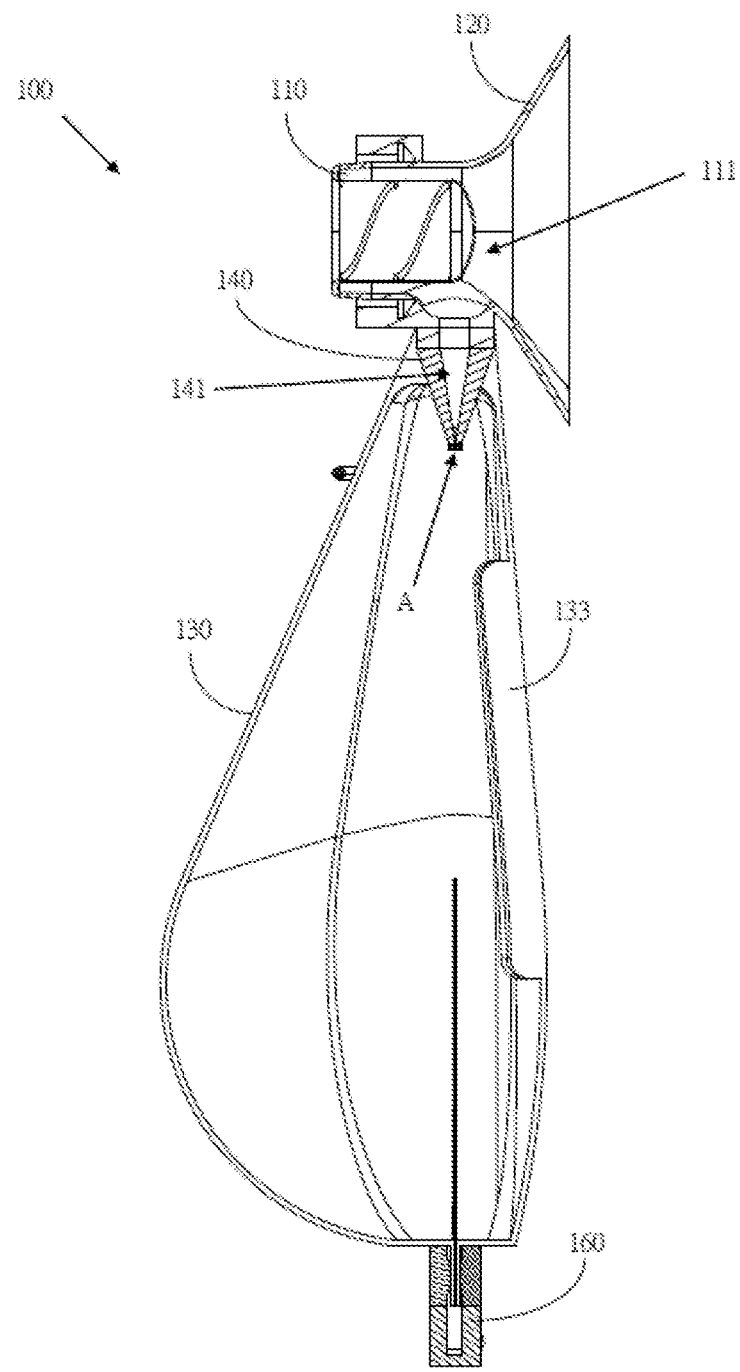
FIG. 1 is a first sectional diagram of the first embodiment of the concealable breast pumping device in the present disclosure.
Figure 2:
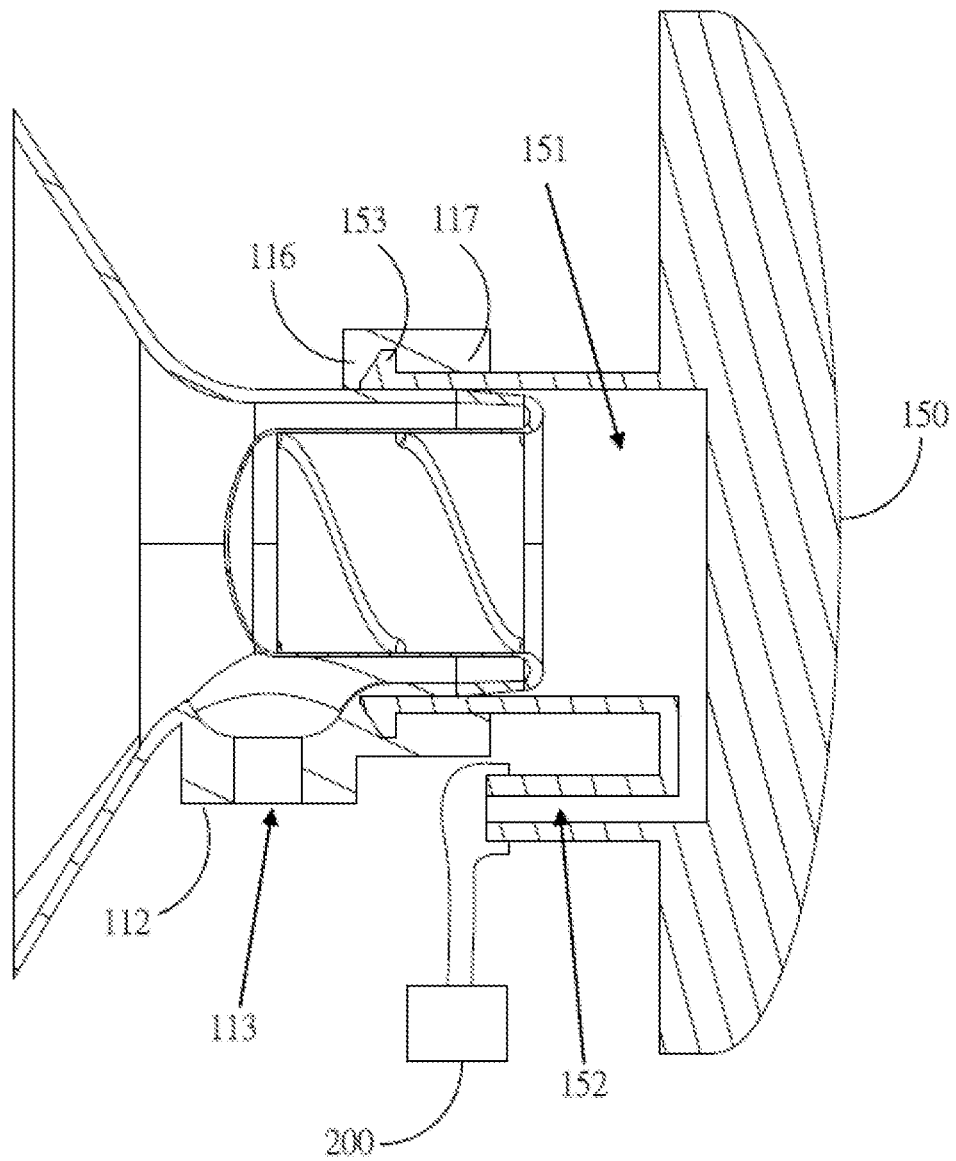
FIG. 2 is a second sectional diagram of the first embodiment of the concealable breast pumping device in the present disclosure.
Figure 3:
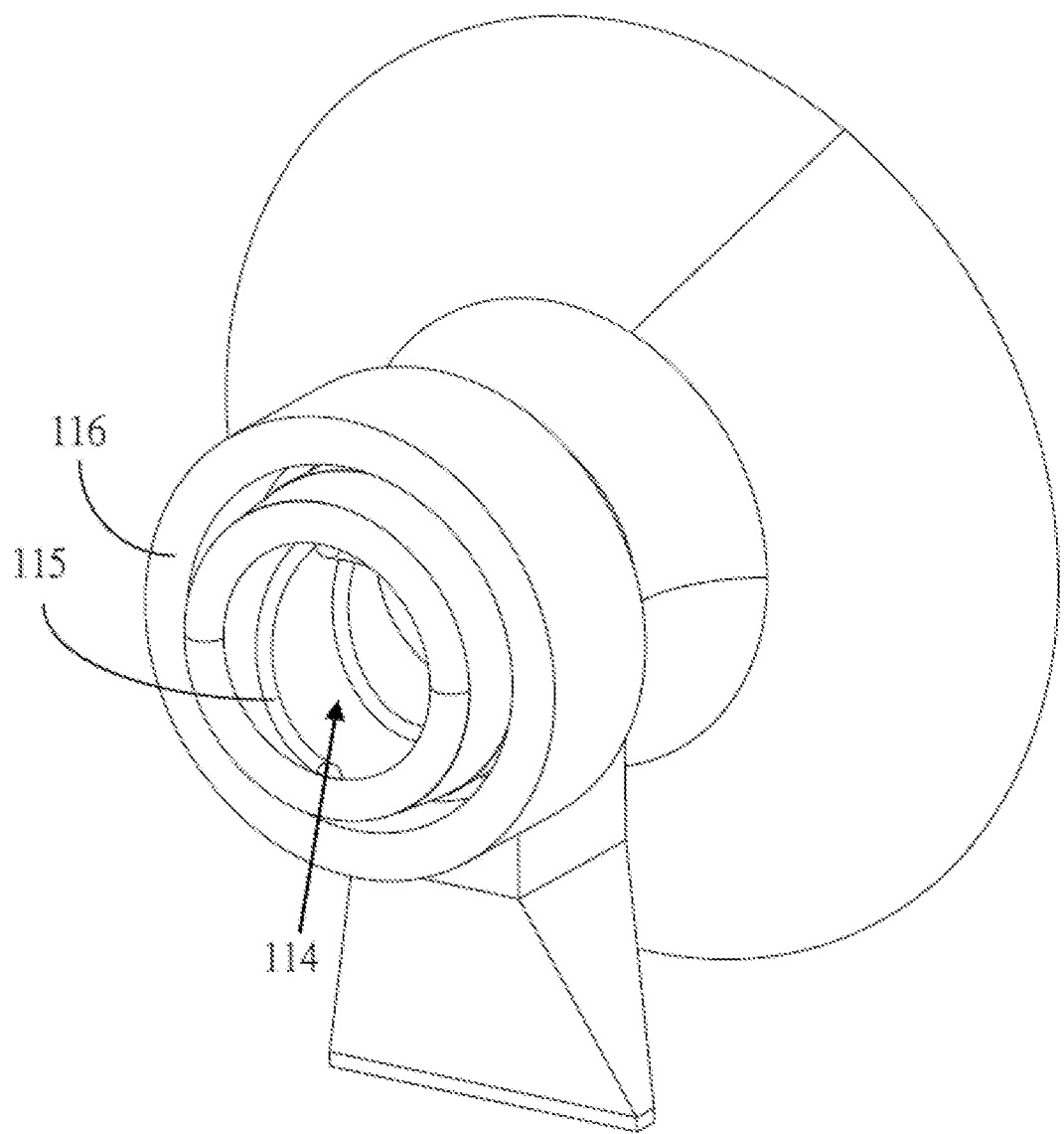
FIG. 3 is a first schematic diagram of the first embodiment of the concealable breast pumping device in the present disclosure.
Figure 4:
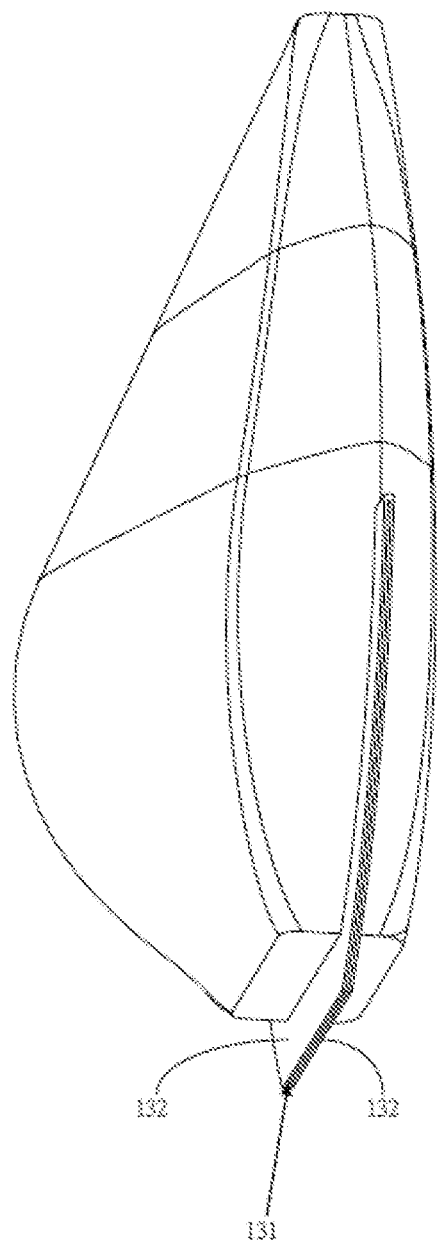
FIG. 4 is a second schematic diagram of the first embodiment of the concealable breast pumping device in the present disclosure.
Figure 5:
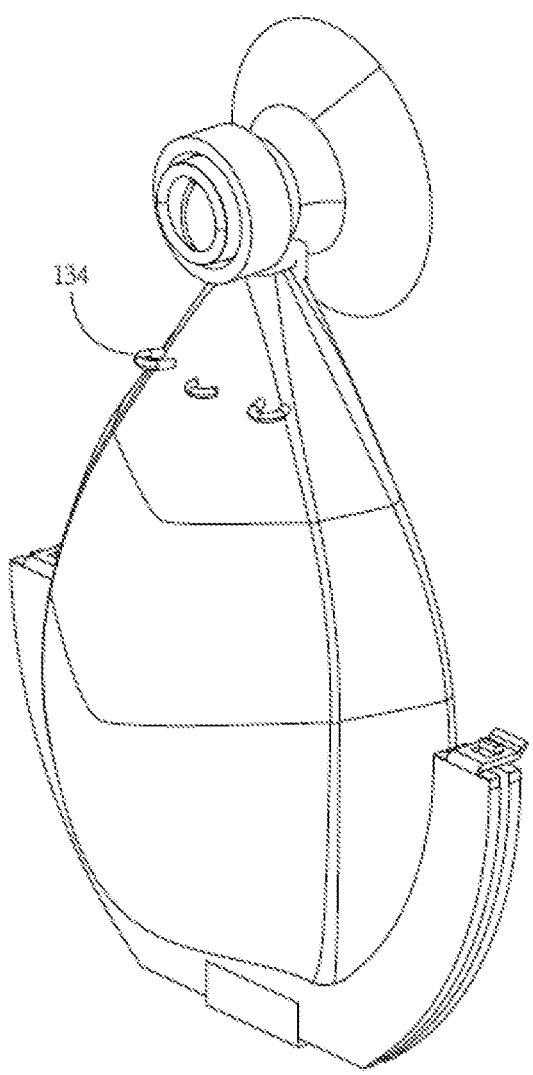
FIG. 5 is a third schematic diagram of the first embodiment of the concealable breast pumping device in the present disclosure.

Please refer to FIG. 1 to FIG. 5; FIG. 1 is the first sectional diagram of the first embodiment of the concealable breast pumping device in the present disclosure, FIG. 2 is a second sectional diagram of the first embodiment of the concealable breast pumping device in the present disclosure; FIG. 3 is a first schematic diagram of the first embodiment of the concealable breast pumping device in the present disclosure; FIG. 4 is a second schematic diagram of the first embodiment of the concealable breast pumping device in the present disclosure; FIG. 5 is a third schematic diagram of the first embodiment of the concealable breast pumping device in the present disclosure. As shown, the concealable breast pumping device 100 in the present disclosure includes a primary unit 110, a squeezing unit 120, a milk collection bag 130, a stop valve unit 140, and a driving unit 150. Wherein, the primary unit 110, the squeezing unit 120, the milk collection bag 130, and the stop valve unit 140 may be structurally integrated. Moreover, the primary unit 110, the squeezing unit 120, milk collection bag 130, and the stop valve unit 140 are made of silica gel.

One end of the primary unit 110 is concaved inward to form a channel 111. An outer edge of the primary unit 110 extends outward to form a protruding portion 112. The protruding portion 112 has a port 113. The port 113 communicates with the channel 111. A center of the other end of the primary unit 110 is concaved inward to form a concave portion 114. An inner wall of the concave portion 114 has a spiral convex portion 115. The squeezing unit 120 is regarded as a cover body structure and covered on one end of the primary unit 110.

One end of the milk collection bag 130 is connected to the protruding portion 112. The other end has an opening 131. Two sides of the opening 131 respectively extend to form two extending portions 132. The two extending portions are gripped by a gripping tool 160 selectively.

The stop valve unit 140 is positioned in the milk collection bag 130 and one end of the stop valve unit 140 is connected to the protruding portion 112. The other end has a gap A, and the gap A is able to opened and closed movably. The stop valve unit 140 has a flow path 141. One end of the flow path 141 communicates with the port 113, and the other end communicates with the gap A.

The main body of the driving unit 150 respectively extends outward to form an engaging portion 151 and a controlling portion 152. The engaging portion 151 and the controlling portion 152 are hollow structures. The inside of the engaging portion 151 communicates with the inside of the controlling portion 152. The engaging portion 151 is detachably jointed with the other end of the primary unit 110. The controlling portion 152 is connected to an external device 200. Wherein, one side of the squeezing unit 120 facing away from the primary unit 110 may convexly be formed to have a plurality of pressure-offsetting portions.

Furthermore, when an internal gas of the controlling portion 152 and the engaging portion 151 is extracted by the external device 200, one end of primary unit 110 is shifted toward the inside of the engaging portion 151 and drives the squeezing unit 120 to generate a contraction. In contrast, when the controlling portion 152 and the inside of the engaging portion 151 are pressure-released by the external device 200 to supply gas, one end of the primary unit 110 is shifted toward an outside of the engaging portion 151 and drives the squeezing unit 120 to generate an expansion. Wherein, by a center of the other end of the primary unit 110 being concaved inward to form a concave portion 114, an inner wall of the concave portion 114 has a spiral convex portion 115 to strengthen the structure to restore one end of the primary unit 110 to the original position.

Specifically, when using the concealable breast pumping device 100 in the present disclosure, the users may cover the area of an areola with the squeezing unit 120 with the protruding portion 112 facing downward. Next, in the process of milking, the pump of the external device 200 performs pumping to extract air from the inside of the controlling portion 152 and the inside of the engaging portion 151 to make the inside of both portions form a negative pressure to further drive one end of the primary unit 110 toward the inside of the engaging portion 151 and drive the squeezing unit to perform a contraction in such a way that the inside of the area of the covered areola forms a negative pressure correspondingly, thus generating the milking function. In the meantime, the squeezing unit 120 has a plurality of pressure-offsetting portions, and the pressure-offsetting portions may perform a squeeze to a breast due to the action of the squeezing unit 120 to increase the effect of milking. The squeezed milk flows into the flow path 141 via the channel 111 and is first stored in the protruding portion 112 and the flow path 141.

It is worth mentioning that the gap A of the stop valve unit 140 is tightly closed so that air is not able to pass through while generating a negative pressure in the inside of the area of the areola covered by the squeezing unit 120. Wherein, when a negative pressure exists in the channel 111, the effect of milking also occurs. Therefore, it is faster to obtain milk with the structure of the squeezing unit 120 for squeezing the breast.

When a squeeze is completed again, the pressure-relieving valve of the external device 200 imports air into the inside of the controlling portion 152 and the inside of the engaging portion 151 through the controlling portion 152 so that the inside of the controlling portion 152 and the inside of the engaging portion 151 is restored to a massive air pressure. At the moment, one end of the primary unit 110 is shifted toward the outside of the engaging portion 151 when the negative pressure is eliminated, which makes the squeezing unit 120 expand instead of squeezing the area of the areola and further allows the plurality of pressure-offsetting portions not to squeeze the breast. After the inside of the area of the areola covered by the squeezing unit 120 is restored to a massive air pressure, the gap A of the stop valve unit 140 changes from a tightly closed state to a partially or fully open state, making the milk in the protruding portion 112 and the flow channel 141 flow into the milk collection bag 130 via the gap A. After the completion of the process of milking, removing the gripping tool 160 that grips the two extending portions 132 or opening the port of the gripping tool 160 allows milk to flow out from the opening 131 of the milk collection bag 130 for the users to collect the milk. In addition, the inside of the milk collection bag 130 may also be cleaned after the gripping tool 160 is removed.

Furthermore, the flow path 141 is in a conical shape, and the stop valve 140 has one end of the gap A in a flat shape. Nonetheless, the aforementioned descriptions are only explained as examples and not restricted thereto.

In addition, an inner wall on one side of the milk collection bag 130 has a plurality of strip structures 133. When installed on the inner side of a underwear, the milk collection bag 130 would be revealed from the lower position. Therefore, a small part would be tightened. To allow the milk to flow smoothly to the bottom of the milk collection bag, these strip structures 133 are needed for space expansion.

In addition, an outer wall on one side of the milk collection bag 130 has a plurality of hook rings 134 which are used to connect the silica gel to the outer cover so as to have positioning effectiveness that allows the users to use conveniently when the milk collection bag is fixed to the outer cover (including the driving unit).

Specifically, the outer edge of the primary unit 110 may protrude outward to form a joint portion 116, and the inner wall of the joint portion 116 protrudes toward the primary unit 110 to form a positioning structure 117. Furthermore, the outer edge of the engaging portion 151 of the driving unit 150 may correspond to the positioning structure 117 to form a fastening structure 153. Therefore, when the engaging portion 151 of the driving unit 150 is engaged with the engaging portion 116 of the other end of the primary unit 110, the fastening structure 153 and the positioning structure 117 may be fastened to each other to make the engaging portion 151 and the joint portion 116 of the primary unit 110 joint tightly to further make the engaging portion 151 form a sealed vacuum state.

Figure 6:
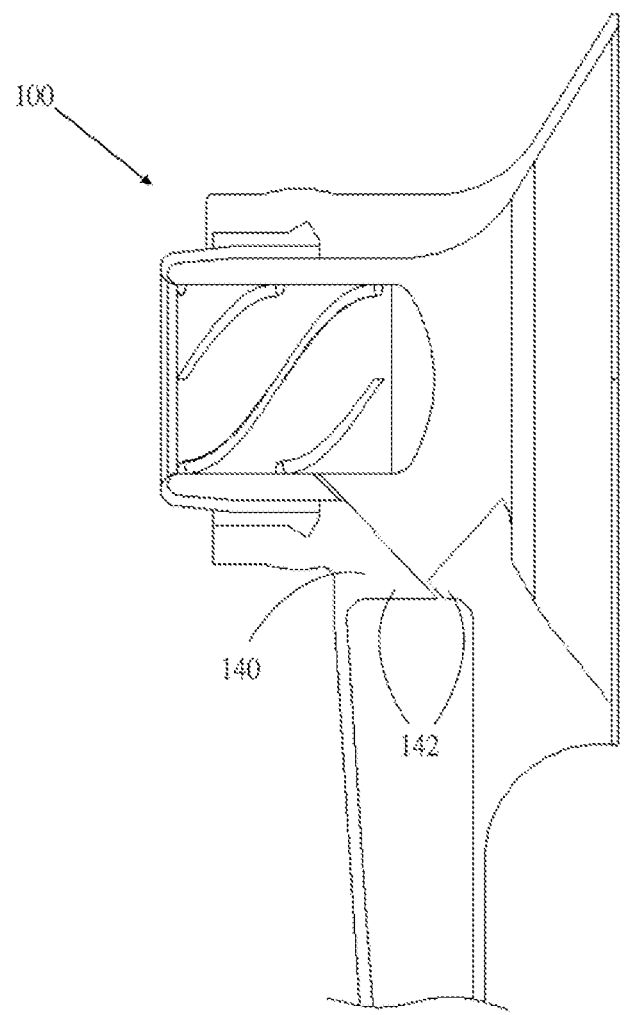
FIG. 6 is a sectional diagram of second embodiment of the concealable breast pumping device in the present disclosure.

Please refer to FIG. 6, illustrating the sectional diagram of second embodiment of the concealable breast pumping device in the present disclosure. As shown, the major difference from the first embodiment as described above is that the stop valve unit 140 is the structure formed by parts of two convex portions 142 overlapping each other, and the gap A is in the between of the two convex portions 142. Nonetheless, the aforementioned descriptions are only explained as examples and not restricted thereto.

As stated, the concealable breast pumping device in the present disclosure is designed by the integration of four components, namely the primary unit, the squeezing unit, the milk collection bag, and the stop valve unit, making the pumping device easy to clean by users. Moreover, under the condition of an integrated design that miniaturizes the volume, users may use the pumping device on their breasts at anytime and anywhere, largely enhancing the users' convenience at using the pumping device.

The embodiments as described above are only explanations of the technical ideas and features of the present disclosure. The purpose is to enable those skilled in the art to understand the contents in the present disclosure and put the contents into practice. It is apparent that the claims of the present disclosure cannot be confined by the contents. That is, the scopes of the equivalent changes or modifications made by the spirit disclosed by the present disclosure should still be included in the claims of the present disclosure.

What is claimed is:

1. A concealable breast pumping device, comprising:
a primary unit, one end thereof concaved inward to form a channel; wherein, an outer edge of the one end of the primary unit extends outward to form a protruding portion, the protruding portion has a port, the port communicates with the channel, a center of an other end of the primary unit is concaved inward to form a concave portion, and an inner wall of the concave portion has a spiral convex portion;
a squeezing unit, also regarded as a cover body structure, covered on the one end of the primary unit near the protruding portion;
a milk collection bag, one end thereof connected to the protruding portion, and an other end having a opening; wherein, two sides of the opening respectively extend to form two extending portions, and the two extending portions are gripped by a gripping tool selectively;
a stop valve, positioned in the milk collection bag and one end of the stop valve connected to the protruding portion; wherein an other end has a gap, the gap is able to opened and closed movably, the stop valve has a flow path, one end of the flow path communicates with the port, and an other end communicates with the gap; and
a driving unit, a main body thereof respectively extending outward to form an engaging portion and a controlling portion; wherein, the engaging portion and the controlling portion are hollow structures, an inside of the engaging portion communicates with an inside of the controlling portion, the engaging portion is detachably jointed with the other end of the primary unit, and the controlling portion is connected to an external device.

2. The concealable breast pumping device according to claim 1, wherein when an internal gas of the controlling portion and the engaging portion is extracted by the external device, the one end of primary unit is shifted toward the inside of the engaging portion and drives the squeezing unit to generate a contraction.

3. The concealable breast pumping device according to claim 2, wherein when the controlling portion and the inside of the engaging portion are pressure-released by the external device to supply gas, the one end of the primary unit is shifted toward an outside of the engaging portion and drives the squeezing unit to generate an expansion.

4. The concealable breast pumping device according to claim 1, wherein the primary unit, the squeezing unit, the milk collection bag, and the stop valve are integrated.

5. The concealable breast pumping device according to claim 4, wherein the primary unit, the squeezing unit, the milk collection bag, and the stop valve are made of silica gel.

6. The concealable breast pumping device according to claim 1, wherein the flow path is in a conical shape.

7. The concealable breast pumping device according to claim 1, wherein the other end of the stop valve is in a flat shape.

8. The concealable breast pumping device according to claim 1, wherein an inner wall on one side of the milk collection bag has a plurality of strip structures.

9. The concealable breast pumping device according to claim 1, wherein an outer wall on one side of the milk collection bag has a plurality of hook rings.

* * * * *